(12) United States Patent
Sachdeva et al.

(10) Patent No.: US 9,867,827 B1
(45) Date of Patent: Jan. 16, 2018

(54) METHODS AND FORMULATIONS FOR TOPICAL TREATMENT OF PSORIASIS

(71) Applicant: Florida A&M University, Tallahassee, FL (US)

(72) Inventors: Mandip Sachdeva, Tallahassee, FL (US); Ketankumar Patel, Tallahassee, FL (US)

(73) Assignee: Florida A&M University, Tallahassee, FL (US)

( * ) Notice: Subject to any disclaimer, the term of this patent is extended or adjusted under 35 U.S.C. 154(b) by 0 days.

(21) Appl. No.: 15/250,175

(22) Filed: Aug. 29, 2016

Related U.S. Application Data

(60) Provisional application No. 62/210,715, filed on Aug. 27, 2015.

(51) Int. Cl.
| | | |
|---|---|---|
| *A61K 31/519* | (2006.01) | |
| *A61K 31/7088* | (2006.01) | |
| *C12N 15/113* | (2010.01) | |
| *A61K 9/00* | (2006.01) | |
| *A61K 47/18* | (2017.01) | |
| *A61K 47/22* | (2006.01) | |
| *A61K 47/48* | (2006.01) | |

(52) U.S. Cl.
CPC .......... *A61K 31/519* (2013.01); *A61K 9/0014* (2013.01); *A61K 31/7088* (2013.01); *A61K 47/18* (2013.01); *A61K 47/22* (2013.01); *A61K 47/48046* (2013.01); *C12N 15/1136* (2013.01); *C12N 2310/14* (2013.01); *C12N 2310/3515* (2013.01); *C12N 2320/31* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 6,440,465 B1 | 8/2002 | Meisner | |
| 2009/0253777 A1* | 10/2009 | Hanauske-Abel | C07K 14/4702 514/44 R |
| 2011/0038965 A1* | 2/2011 | McKay | A61K 31/14 424/742 |
| 2011/0098267 A1 | 4/2011 | Babu et al. | |
| 2012/0142755 A1* | 6/2012 | Lecron | A61K 8/64 514/44 A |
| 2014/0031312 A1* | 1/2014 | Chatterji | A61K 9/0014 514/54 |

FOREIGN PATENT DOCUMENTS

| | | |
|---|---|---|
| EP | 873047971 A1 | 2/1987 |
| WO | 2006049442 A1 | 5/2006 |
| WO | 2009100406 A3 | 11/2009 |

OTHER PUBLICATIONS

Bruner et al, A Systematic Review of Adverse Effects Associated with Topical Treatments for Psoriasis, Dermatology Online Journal, 2003, pp. 1-4.
Stein, Clinical studies of a new vehicle formulation for topical corticosteroids in the treatment of psoriasis, J Am Acad Dermatol, July 2005, pp. 1-11.
Eskicirak et al., The treatment of psoriasis vulgaris: 1% topical methotrexate gel, International Journal of Dermatology 2006, vol. 45, pp. 965-969.

* cited by examiner

*Primary Examiner* — Tracy Vivlemore
(74) *Attorney, Agent, or Firm* — Nilay J. Choksi; Smith & Hopen, P.A.

(57) ABSTRACT

A pharmaceutical formulation and topical administration thereof for the treatment of psoriasis or any one or more symptoms associated therewith. The formulation contains a therapeutically effective amount pemetrexed alone as the active agent or can contain therapeutically effective amounts of pemetrexed in combination with siRNA-inhibiting TNFα. The formulation may further include a cationic surfactant, such as cetylpyridinum chloride, and urea for enhanced permeation through the stratum corneum of the patient or subject.

9 Claims, 6 Drawing Sheets

METHODS AND FORMULATIONS FOR TOPICAL TREATMENT OF PSORIASIS

CROSS-REFERENCE TO RELATED APPLICATIONS

Figure 1A:
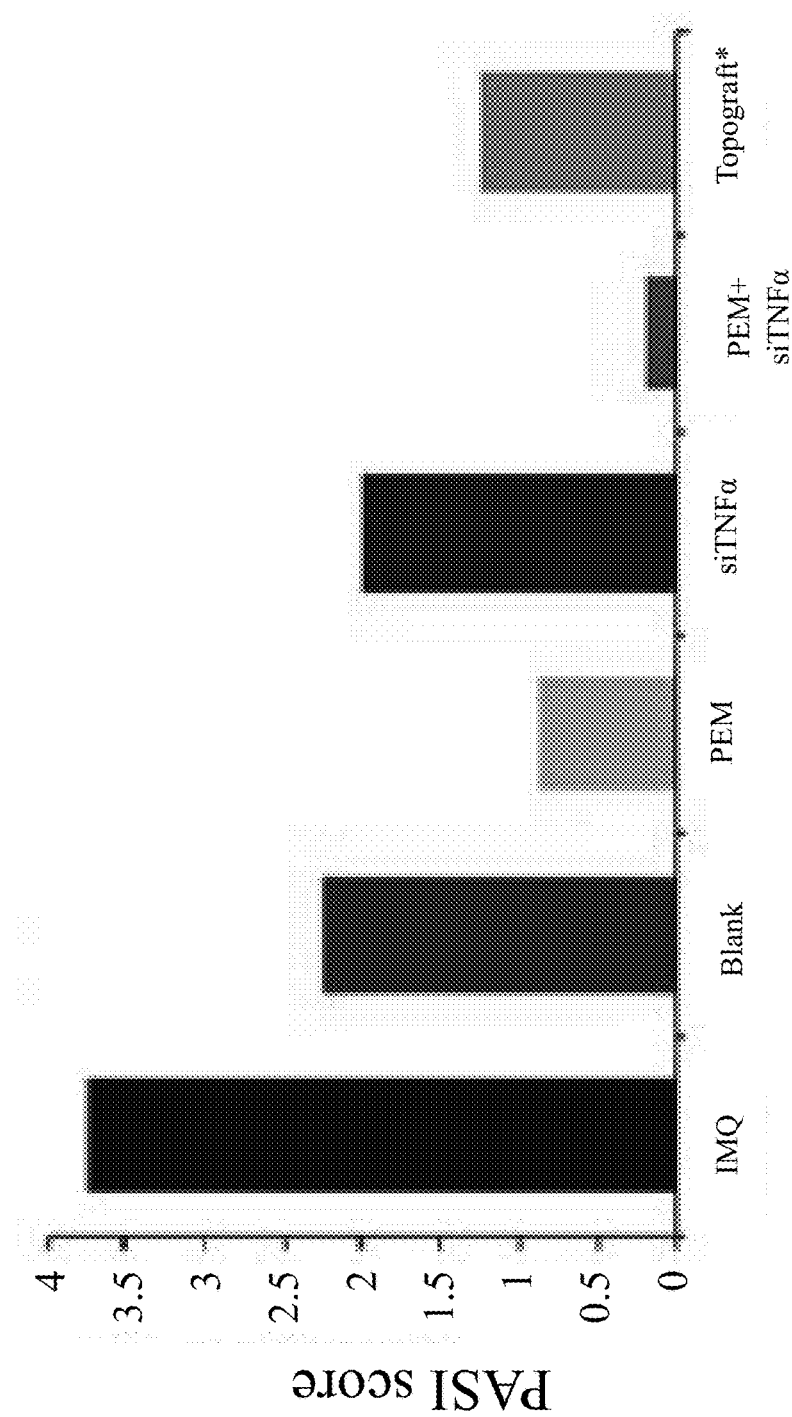

This nonprovisional application claims priority to U.S. Provisional Application No. 62/210,715, entitled "Formulations for the Topical Treatment of Psoriasis", filed Aug. 27, 2015 by the same inventors, the entirety of which is incorporated herein by reference.

BACKGROUND OF THE INVENTION

1. Field of the Invention

This invention relates, generally, to pharmaceuticals. More specifically, it relates to formulations for the topical treatment of psoriasis.

2. Brief Description of the Prior Art

Psoriasis is a common, chronic, inflammatory disease with a wide range of clinical presentations. Severity of the disease ranges from mild to severe. Topical corticosteroids are the recommended first-line therapy for short-term use. Response to treatment is quick, but the side effects—such as atrophy, striae, telangiectasias and tachyphylaxis—limits the duration of use.

Topical treatments for psoriasis are known in the art. Examples include PCT Patent Application No. PCT/US2009/033495; U.S. Pat. No. 6,440,465; PCT Patent Application No. PCT/KR2005/003698; European Patent Application No. EP19870304797; Bruner C R et al., A systematic review of adverse effects associated with topical treatments for psoriasis. Dermatol Online J., 9(1): 2, February 2003; Stein L., Clinical studies of a new vehicle formulation for topical corticosteroids in the treatment of psoriasis. J Am Acad Dermatol, 53(1 Suppl 1):S39-49, July 2005; and Eskicirak et al, The treatment of psoriasis vulgaris: 1% topical methotrexate gel. Int J Dermatol, 45(8): 965-969, August 2006. However, none have taught a completely safe and effective topical therapy for treatment of psoriasis and other skin-related immune diseases, while also providing for effectual skin permeation.

Inhibition of tumor necrosis factor (TNF, TNFα, or TNF alpha) is known to be an important factor in reducing the severe symptoms of psoriasis, due in part to its involvement in multiple pathways that promote psoriasis. Extreme hydrophilicity of psoriatic epidermis models and TNFα pose a great challenge in their topical delivery. Due to the lipidic composition of the stratum corneum (outermost layer of skin), transport of hydrophilic molecules to the dermis layer can be very difficult.

Accordingly, what is needed is an improved, more effective pharmaceutical therapy for psoriasis. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an improved therapy for psoriasis is now met by a new, useful, and nonobvious invention.

In an embodiment, the current invention is a method of treating psoriasis in a patient or subject, comprising topically administering a formulation containing a therapeutically effective amount of pemetrexed, wherein the topical administration is performed by applying the formulation onto a psoriatic patch of skin of the patient or subject that is suffering from psoriasis. In other embodiments, the current invention is the formulation itself for topical treatment of psoriasis in the patient or subject, where the formulation comprises a therapeutically effective amount of pemetrexed.

Optionally, the formulation can also include a therapeutically effective amount of siRNA-inhibiting TNFα in combination with the pemetrexed. In a further embodiment, the formulation further includes a fusogenic nanocarrier bound to the siRNA-inhibiting TNFα to internalize and transfect the siRNA-inhibiting TNFα.

To enhance permeation of pemetrexed and/or siRNA-inhibiting TNFα, the formulation can include a cationic surfactant (e.g., cetylpyridinum chloride) and urea. This would increase skin deposition in the patient or subject by enhancing permeation through the stratum corneum of the patient or subject.

In a separate embodiment, the current invention is a method of reducing one or more symptoms associated with a patient or subject suffering from psoriasis, where these symptoms include erythema, scaling, plaque epidermal thickening, rete ridge elongation, inflammation, and a combination thereof. The method comprises topically administering onto a psoriatic patch of skin of the patient or subject a formulation containing therapeutically effective amounts of pemetrexed, siRNA inhibiting TNFα, urea, and cetylpyridinum chloride as a cationic surfactant. Urea and cetylpyridinum chloride increase permeation of pemetrexed and siRNA inhibiting TNFα through a stratum corneum of the patient/subject for enhanced skin deposition in the patient or subject. The formulation further includes a fusogenic nanocarrier bound to the siRNA-inhibiting TNFα to internalize and transfect the siRNA-inhibiting TNFα.

It is an object of the current invention to provide a stable formulation and methodology allowing significantly higher skin permeation and deposition of pemetrexed and siTNFα to deeper skin layers.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which:

FIG. 1A is a graphical illustration depicting PASI score of pemetrexed and combination treated psoriatic animals.

FIG. 1B is a graphical illustration depicting TEWL of pemetrexed and combination treated psoriatic animals.

FIG. 2 is a graphical illustration depicting skin deposition of various pemetrexed formulations.

FIG. 3 depicts a comparison of the psoriatic plaque seen on mice models: control vs. pemetrexed+siTNFα.

FIG. 4 depicts H&E and IHC of skin samples following in vivo psoriasis studies of control, TOPGRAF, pemetrexed, pemetrexed/siTNFα and siTNFα treated animals.

FIG. 5 depicts western blot analysis of skin samples following in vivo psoriasis studies of control, TOPGRAF, pemetrexed, pemetrexed/siTNFα and siTNFα treated animals.

DETAILED DESCRIPTION OF THE PREFERRED EMBODIMENT

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

In certain embodiment, the current invention is a method of treating psoriasis comprising topically administering a therapeutically effective amount of pemetrexed to a patient or subject. Alternatively, in certain embodiments, the current invention is a topical therapy or formulation comprising a therapeutically effective amount of pemetrexed. In either case, the pemetrexed would be administered topically onto a psoriatic patch of skin, where the psoriatic patch of skin is a section or segment of the patient/subject's skin that is afflicted by or suffering from psoriasis. In certain embodiments, the formulation or agent being administered can include siRNA-inhibiting TNFα (siTNFα), as inhibition of TNFα can be important in reducing the severe symptoms of psoriasis due to its involvement in multiple pathways promoting psoriasis. In alternative or further embodiments, a cationic surfactant and urea can be admixed with the pemetrexed to enhance permeation of pemetrexed through the stratum corneum of the patient or subject.

It was found herein that pemetrexed, which is a known an anticancer agent manufactured by ELI LILLY AND COMPANY under the brand name ALIMTA, is a potential therapeutic candidate for psoriasis; however, pemetrexed has never been investigated for topical delivery or for psoriasis treatment. Pemetrexed is available as a parenteral injection as an anticancer agent, but systemic toxicity and patient compliance are significant obstacles for its use in psoriasis. Further, pemetrexed and siTNFα are hydrophilic molecules. Therefore, they have minimal permeability through skin, which has limited their application in psoriasis.

In general, studies have shown that 70% of patients with psoriasis prefer topical therapy as the treatment of choice, and as such, a more effective topical therapy was sought. In such a scenario, a topical formulation and administration of pemetrexed—individually or in combination with siTNFα—is a novel and extremely beneficial approach for psoriasis treatment.

Study/Example

Objectives of the current study were to explore a synergistic therapeutic strategy targeting TH17/IL23 axis for the treatment of psoriasis and to develop a suitable formulation to deliver hydrophilic small/macromolecules across stratum corneum to overcome skin barrier. Various formulation strategies were developed, characterized, and compared to test efficacy and to maximize the skin deposition of both pemetrexed and siTNFα. Concurrently, a fusogenic lipid-based nanocarrier was developed for encapsulating siTNFα. Finally, the optimized formulation was incorporated into urea containing hydrogel. It was ultimately found that topical delivery of a cationic lipid complexation with urea hydrogel-based formulation of pemetrexed and siTNFα is an effective therapeutic option for the treatment of psoriasis.

Methods

In Vivo Imiquimod (IMQ) Induced Psoriatic-Like Plaque Model

An IMQ-induced psoriatic-like plaque model was used to evaluate the effect of pemetrexed, siTNFα, and pemetrexed-siTNFα. Briefly, IMQ cream was applied topically to the shaven dorsal regions of C57BL/6 mice (4 mg/day/animal) to form psoriatic-like plaques. The animals were then treated by applying cetylpyridinum chloride (CPC)-urea gel containing blank formulation as negative control, pemetrexed formulation, siTNFα formulation, pemetrexed-siTNFα combination formulation, or a known tacrolimus cream (TOPGRAF) as a positive control. The CPC-urea gels containing the foregoing formulations were applied to the inflamed dorsal regions of the animals for five (5) consecutive days.

Psoriasis Area Severity Index (PASI) Scoring and Trans-Epidermal Water Loss (TEWL) Determination of Skin A clinical scoring method for the PASI was used daily to score the severity of the inflammation induced on the dorsal regions of the mice, based on the extent of erythema, scaling, and epidermal thickening. The PASI score was assigned daily after initiating treatment on a scale of 0 to 4, where 0 indicated no inflammation, 1 indicated slight inflammation, 2 indicated moderate inflammation, 3 indicated marked inflammation, and 4 indicated very severe inflammation.

The TEWL was estimated using DELFIN VAPOMETER (DELFIN Technologies Ltd, Finland) as a measure of the extent of skin damage and healing with each day of treatment. The device was placed gently on the dorsal region of the mice each day of treatment and the value corresponding to water loss was recorded.

Skin Deposition of Pemetrexed

A further objective of this study was to evaluate permeation and deposition of pemetrexed in skin select an optimal topical delivery system for pemetrexed. Specifically, to determine the extent of skin deposition of pemetrexed solution and its various formulations, skin permeation studies were carried out using dermatomed human skin. The skin was mounted on Franz diffusion cells (PERMEGEAR Inc., Riegelsvilla, Pa., USA), functioning as the membrane between the donor and receptor chambers. The skin was positioned so that the stratum corneum is in direct contact with the donor chambers.

The receptor chamber was filled with PBS (pH 7.4), stirred at 300 rpm and maintained at 32±0.5° C. using a circulating water bath. The studies were carried out for 24 hours under non-occlusive conditions. 150 µL of pemetrexed formulations were applied to the skin in contact with the donor chamber and incubated for 6 hours. Afterwards, the excess formulation was removed from the surface of the skin with a cotton swab, washed with 50% v/v ethanol in water and then blotted dry with lint-free absorbent wipes. The epidermis was removed, and the amount of pemetrexed in the dermal layer was analyzed using HPLC.

Skin Harvesting

At the end of the study, skin samples were harvested and analyzed for inflammatory proteins by immunohistochemistry and western blot analyses.

Generally, gel retardation assay, serum stability, cellular internalization and transfection efficiency of siRNA carrier were determined in A431 skin cancer cells using FITC-siRNA and plasmid GFP. Topical delivery of siRNA was confirmed by fluorescence microscope.

Specifically, hematoxylin and eosin (H&E) staining of the excised skin samples was performed. Briefly, formalin-fixed, paraffin-embedded skin sections were de-paraffinized, rehydrated and stained with hematoxylin and counterstained with eosin. The stained skin sections were mounted and viewed with the OLYMPUS BX40 light microscope equipped with a computer-controlled digital camera (DP71, Olympus Center Valley, Pa.).

Immunohistochemical studies were carried out on paraffin-embedded skin sections using the protocol specified by IMMUNOCRUZ mouse ABC staining kit. Briefly, the section slides were washed in xylene and hydrated in varying concentrations of alcohol. The sections were then incubated with primary antibodies against Ki67 overnight at 4° C. Horseradish peroxidase-conjugated secondary antibody was then applied for the detection of the primary antibody. The section slides were subsequently stained with DAB chromogen and counterstained with hematoxylin. OLYMPUS BX40 microscope equipped with a computer-controlled digital camera was used for the visual analysis of the images of the sections. Positive results were considered for the brown staining of the skin sections.

For western blot analysis, skin samples were minced in lysis cocktail composed of RIPA lysis buffer, protease inhibitor (PI) and phenylmethylsulfonyl fluoride (PMSF). BCA Protein Assay Reagent Kit was used to estimate the protein concentration per the manufacturer's protocol. 50 µg of the extracted protein for each sample was loaded into a gel and subjected to SDS-polyacrylamide electrophoresis (SDS-PAGE). The blots were incubated with primary antibodies for TNFα, NFkB, IL23, IL17, and β-actin and subsequently detected with Horseradish peroxidase-conjugated secondary antibodies using a SUPERSIGNAL WEST PICO Chemiluminescent Substrate (Pierce, Rockford, Ill., USA) and BIORAD CHEMIDOC XRS+ imaging system (Hercules, Calif., USA).

Results

Efficacy of Pemetrexed for Psoriasis Therapy

Figure 1B:
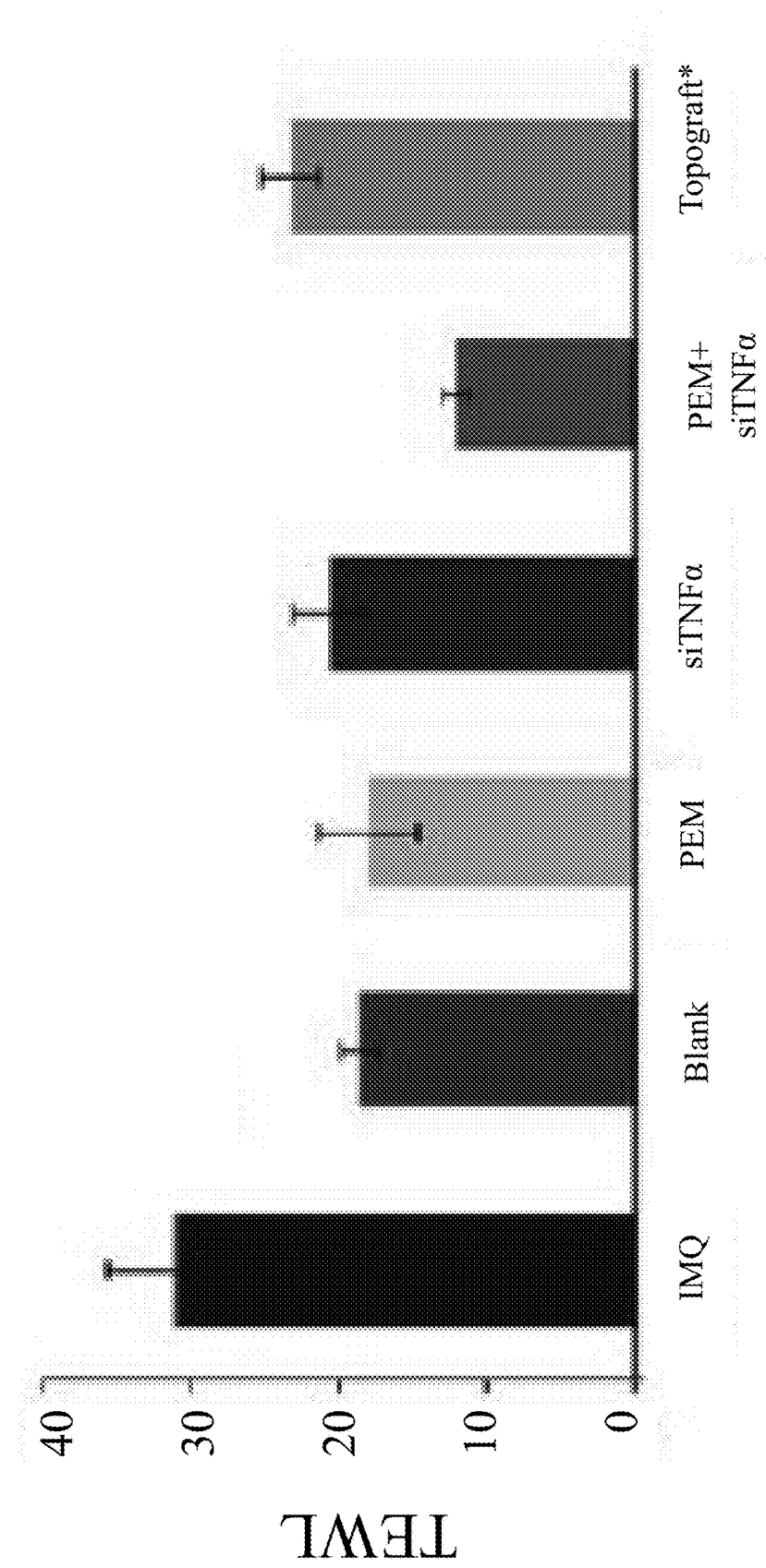
Figure 3:
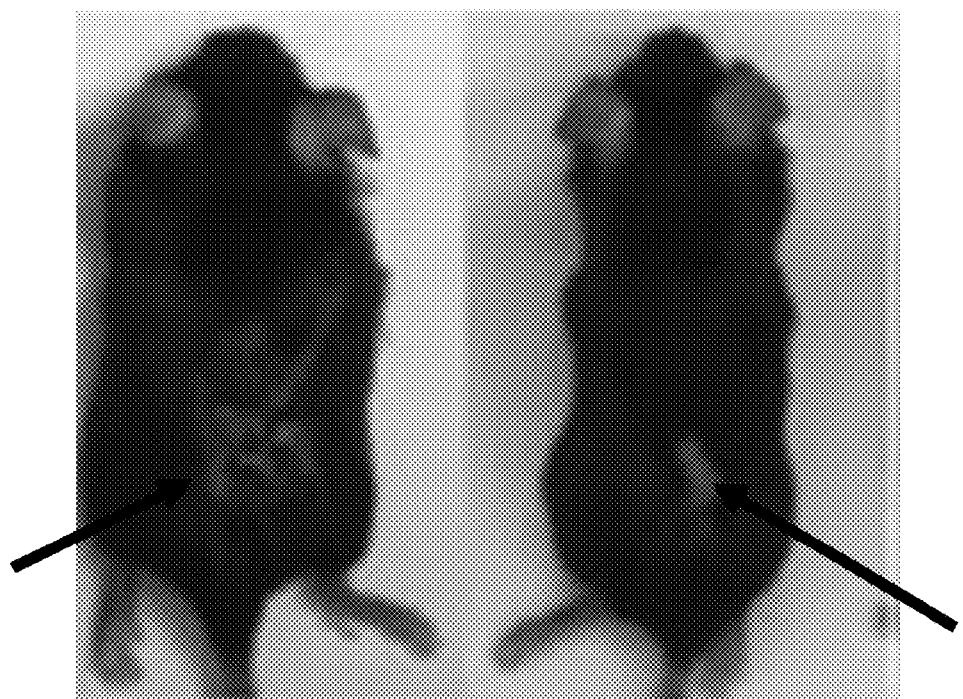

After five (5) treatments, pemetrexed alone and combination-treated groups showed significant reduction in erythema and scaling compared to other groups, as reflected in near to 0 PASI score. In other words, the PASI score was significantly reduced in both pemetrexed and pemetrexed-siTNFα treated groups. As seen in FIGS. 1A, 1B, and -3, both groups showed better PASI score (FIG. 1A), better TEWL (FIG. 1B), and reduction in psoriatic plaque (FIG. 3) compared to the known tacrolimus cream (TOPGRAF).

Figure 4:
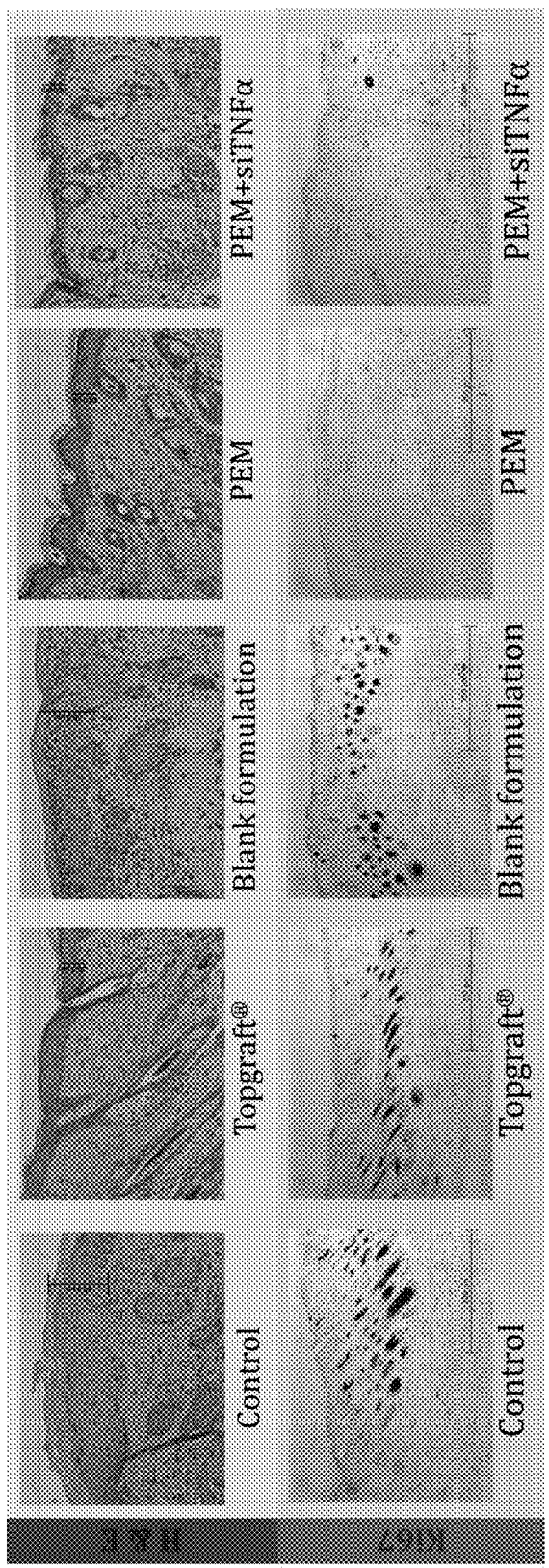

Specifically, the combination-treated group showed significant reduction in erythema and scaling compared to other groups as reflected in 0.2 PASI score ($p<0.01$) (FIG. 1A). The PASI score for pemetrexed alone was superior to that seen with TOPGRAF application, and the combination (pemetrexed-siTNFα) treatment showed complete healing of psoriatic plaque (FIG. 4). Similarly, the TEWL in the blank group, pemetrexed group, and siTNFα group clearly signified the beneficiary role of urea in hydrating psoriatic skin ($p<0.05$) (FIG. 1B).

H&E staining revealed marked reduction and pronounced decrease in epidermal thickening and rete-ridge extension, while immunohistochemical staining (IHC) showed significant reduction in expression of ki67 in the combination group compared to the negative control. Western blot analyses complimented these results and showed significant reduction ($p<0.05$) in the expressions of inflammatory markers, such as TNFα, $NF_KB$, IL23, and IL17 in pemetrexed and pemetrexed-siTNFα treated psoriatic animals, when compared to the TOPGRAF group. Combination treatment showed lower expression than pemetrexed alone.

Additionally, siTNFα was avidly bound to fusogenic nanocarrier and showed internalization and transfection comparable to lipofectamine.

Skin Deposition Study of Pemetrexed

Figure 2:
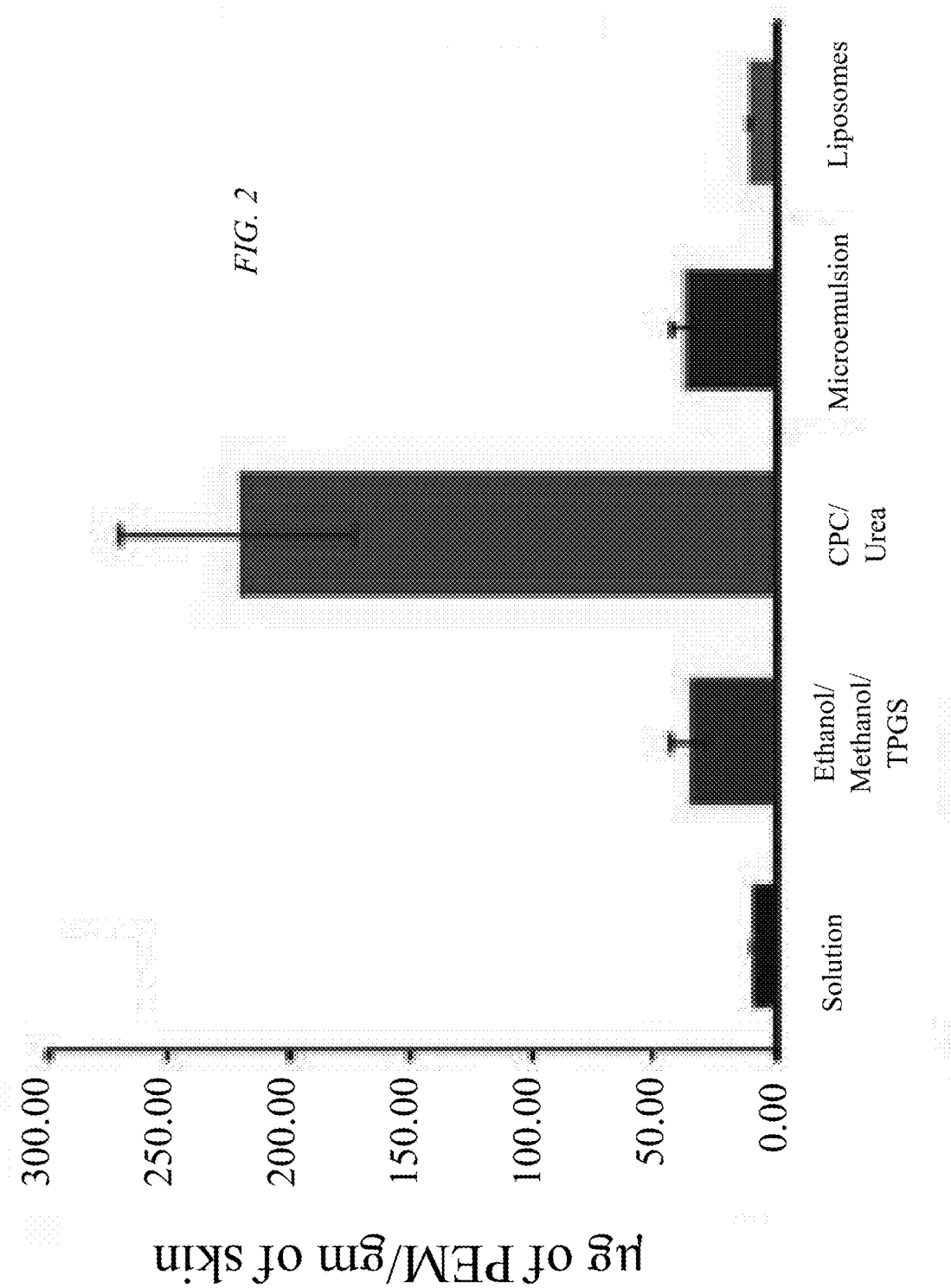

It was found herein that a pemetrexed-CPC ionic complex/urea-based formulation that showed unexpected, remarkably higher skin deposition of pemetrexed compared to menthol-, liposome-, and microemulsion-based formulations. Pemetrexed skin deposition was nearly 26-fold higher compared to plain solution. As seen in FIG. 2, using the methodology described previously, the pemetrexed-CPC complex-based formulation incorporated in urea-containing hydrogel was found to show the highest skin deposition amongst all the formulations.

Harvested Skin

H&E staining revealed extensive epidermal thickening (acantosis), rete-ridge extensions and thickening of the stratum corneum (hyperkeratosis) for the negative control (IMQ-only treatment). These were prominently decreased for pemetrexed/siTNFα, which illustrated similar morphology to the positive control (no IMQ, no treatment) and TOPGRAF (see FIG. 4) but less than either pemetrexed or siTNFα. IHC staining showed markedly reduced brown staining for Ki67 (keratinocyte proliferation marker) for pemetrexed/siTNFα, signifying reduced inflammation, reduced proliferation of keratinocytes, and reduced epidermal thickening (FIG. 4).

Figure 5:
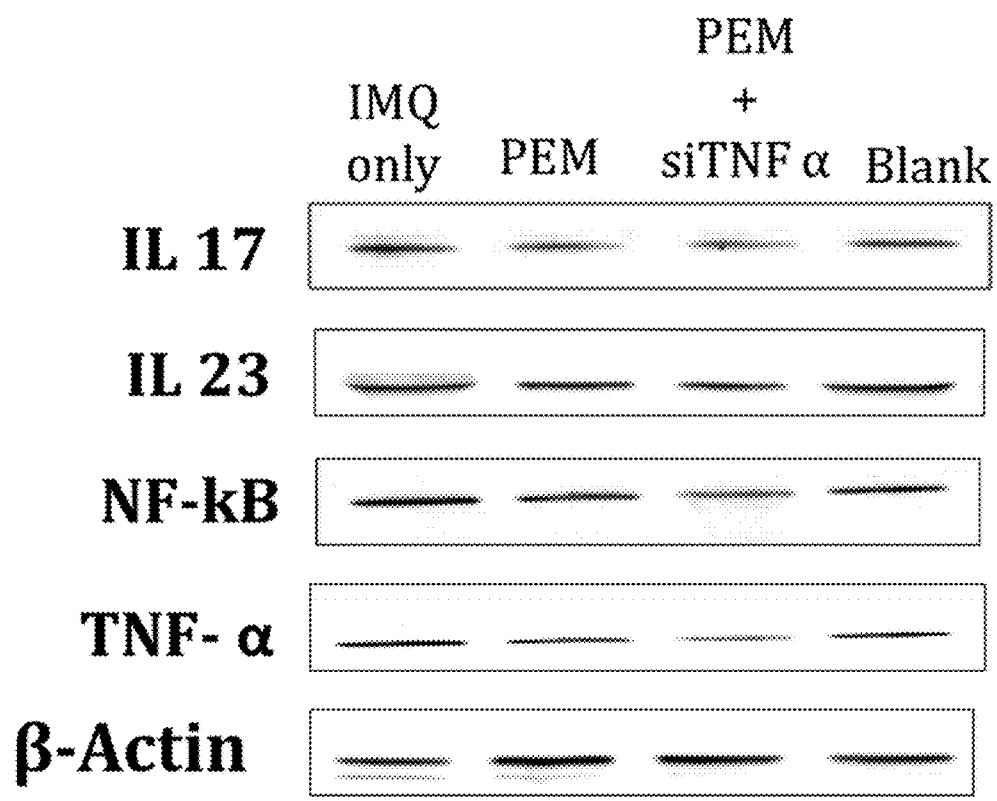

As can be seen in FIG. 5, western blot confirmed the decreased expressions of IL-17 and IL-23 for pemetrexed/siTNFα- and pemetrexed-treated mice, thus revealing the successful inhibition of the IL signaling pathways. Both the treatment groups showed nearly similar inhibition in IL-17 and IL-23 expression. However, there was more significant (p<0.01) reduction of NFκB and TNFα in the combination (pemetrexed/siTNFα) treated group, compared to pemetrexed by itself.

Definitions

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" or "formulation" is intended to encompass a product comprising the specified ingredients, in the specified amounts, as well as any product which results, directly or indirectly, from combination of the specified ingredients in the specified amounts. Generally, the specified ingredients, or pharmaceutically acceptable salts and derivatives thereof, are suitable agents for use in the diagnosis, mitigation, treatment, cure, or prevention of disease in a subject, specifically but not exclusively effective in the treatment of psoriasis, including specifically the treatment of psoriatic plaque, when administered in an effective amount to a subject in need thereof.

As used herein, "patient", "subject" and "subject in need of treatment" are used interchangeably to mean mammals in need of diagnosis or treatment of psoriasis.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers, such as a solvent, suspending agent or vehicle, for delivering the compound or compounds in question to the mammal. The carrier may be liquid or solid and is selected with the planned manner of administration in mind. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, liposomes, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. The carrier can also include any and all other vehicles, coatings, diluents, antibacterial and antifungal agents, isotonic and absorption delaying agents, buffers, carrier solutions, suspensions, colloids, and the like. Formulations are described in a number of sources that are well known and readily available to those skilled in the art. Except insofar as any conventional media or agent is incompatible with the active ingredient, its use in the therapeutic compositions is contemplated. For example, *Remington's Pharmaceutical Sciences* (Martin E W [1995] Easton Pa., Mack Publishing Company, 19$^{th}$ ed.) describes formulations which can be used in connection with the subject invention.

As used herein, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

A "safe and effective amount" refers to the quantity of a component or composition that is sufficient to yield a desired therapeutic response without undue adverse side effects (such as toxicity, irritation, or allergic response) commensurate with a reasonable benefit/risk ratio when used in the manner of this invention for the treatment of psoriasis.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to psoriasis or other skin-related immune diseases, an effective amount comprises an amount sufficient to cause plaque to shrink or heal and/or to decrease the growth rate of the plaque (such as to suppress plaque growth). In some embodiments, an effective amount is an amount sufficient to delay development. In some embodiments, an effective amount is an amount sufficient to prevent or delay occurrence and/or recurrence. An effective amount can be administered in one or more doses.

As used herein, "treatment" refers to obtaining beneficial or desired clinical results, or any measurable mitigation of disease in a subject, including resolution, reduction, halting progression, and/or slowing progression of a disease. Beneficial or desired clinical results include, but are not limited to, any one or more of the following: alleviation of one or more symptoms (such as plaque growth), diminishment of extent of psoriasis, stabilized (i.e., not worsening) state of psoriasis, preventing or delaying spread (e.g., metastasis) of the plaque, preventing or delaying occurrence or recurrence of psoriasis, delay or slowing of psoriasis progression, amelioration of the psoriatic state. It is contemplated that these same benefits may apply to other skin-related immune diseases as well. The methods of the invention contemplate any one or more of these aspects of treatment.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method of treating psoriasis in a patient or subject, comprising topically administering a formulation containing a therapeutically effective amount of pemetrexed, wherein the formulation further includes a therapeutically effective amount of siRNA-inhibiting TNFα in combination with said pemetrexed, wherein said topical administration is performed by applying said formulation onto a psoriatic patch of skin of said patient or subject that is suffering from psoriasis.

2. A method as in claim 1, wherein the formulation further includes a fusogenic nanocarrier bound to said siRNA-inhibiting TNFα to internalize and transfect said siRNA-inhibiting TNFα.

3. A method as in claim 1, wherein the formulation includes a cationic surfactant and urea for enhancing permeation of said pemetrexed through a stratum corneum of said patient or subject and for enhanced skin deposition in said patient or subject.

4. A method as in claim 3, wherein said cationic surfactant includes cetylpyridinum chloride.

5. A formulation for topical treatment of psoriasis in a patient or subject, comprising a therapeutically effective amount of pemetrexed and a therapeutically effective amount of siRNA-inhibiting TNFα in combination with said pemetrexed.

6. A formulation as in claim 5, further comprising a fusogenic nanocarrier bound to said siRNA-inhibiting TNFα to internalize and transfect said siRNA-inhibiting TNFα.

7. A formulation as in claim 5, further comprising a cationic surfactant and urea for enhancing permeation of said pemetrexed through a stratum corneum of said patient or subject and for enhanced skin deposition in said patient or subject.

8. A formulation as in claim 7, wherein said cationic surfactant includes cetylpyridinum chloride.

9. A method of reducing one or more symptoms associated with a patient or subject suffering from psoriasis, where said one or more symptoms are selected from the group consisting of erythema, scaling, plaque epidermal thickening, rete ridge elongation, inflammation, and a combination thereof, the method comprising topically administering to said patient or subject a formulation containing therapeutically effective amounts of pemetrexed, siRNA inhibiting TNFα, urea, and cetylpyridinum chloride as a cationic surfactant, wherein said urea and said cetylpyridinum chloride increase permeation of said pemetrexed and said siRNA inhibiting TNFα through a stratum corneum of said patient or subject for enhanced skin deposition in said patient or subject, wherein said formulation further includes a fusogenic nanocarrier bound to said siRNA-inhibiting TNFα to internalize and transfect said siRNA-inhibiting TNFα, wherein said topical administration is performed by applying said formulation onto a psoriatic patch of skin of said patient or subject that is suffering from psoriasis.

* * * * *